United States Patent
Kuyler et al.

(10) Patent No.: US 12,156,814 B2
(45) Date of Patent: Dec. 3, 2024

(54) RETENTION SYSTEM AND METHOD

(71) Applicant: WARSAW ORTHOPEDIC INC., Warsaw, IN (US)

(72) Inventors: Adriaan J. Kuyler, Germantown, TN (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 70 days.

(21) Appl. No.: 17/899,070

(22) Filed: Aug. 30, 2022

(65) Prior Publication Data

US 2022/0409380 A1     Dec. 29, 2022

Related U.S. Application Data

(62) Division of application No. 16/395,880, filed on Apr. 26, 2019, now Pat. No. 11,497,609.

(51) Int. Cl.
*A61F 2/44* (2006.01)
*A61F 2/30* (2006.01)

(52) U.S. Cl.
CPC ........ *A61F 2/30749* (2013.01); *A61F 2/4455* (2013.01)

(58) Field of Classification Search
CPC ............... A61F 2/4455; A61F 2/30405; A61F 2/30749; A61B 17/8052; A61B 17/8625; A61B 17/8635; A61B 17/8695; A61B 17/7032; A61B 17/7049
See application file for complete search history.

(56) References Cited

U.S. PATENT DOCUMENTS

| | | |
|---|---|---|
| 1,016,897 A | 2/1912 | Catherine |
| 1,250,748 A | 12/1917 | Irving |
| 1,697,118 A | 1/1929 | Hoke |
| 1,798,604 A | 3/1931 | Hoke |
| 1,828,856 A | 10/1931 | Bridges |
| 1,884,973 A | 10/1932 | Hoke |

(Continued)

FOREIGN PATENT DOCUMENTS

| | | |
|---|---|---|
| CN | 107913098 A | 4/2018 |
| CN | 106999288 A | 4/2020 |

(Continued)

OTHER PUBLICATIONS

European Patent Office, 80298 Munich, Germany, Supplementary European Search Report, Application No. 20794881, Date: Apr. 6, 2023.

(Continued)

*Primary Examiner* — Anu Ramana
(74) *Attorney, Agent, or Firm* — Sorell, Lenna & Schmidt, LLP

(57) ABSTRACT

A retention system includes a first member having an inner surface defining a first thread form. The first thread form includes a first stage having a first pitch and a second stage having a second pitch that is greater than the first pitch. A second member includes a shaft and a neck. The shaft includes an outer surface defining a second thread form configured to engage the first thread form to lock the second member with the first member. The neck includes a smooth unthreaded section. Methods of use are disclosed.

19 Claims, 13 Drawing Sheets

(56) References Cited

U.S. PATENT DOCUMENTS

| | | |
|---|---|---|
| 1,905,869 A | 4/1933 | Hoke |
| 2,367,213 A | 1/1945 | Harding |
| 2,581,690 A | 1/1952 | Moehle et al. |
| 2,842,180 A | 7/1958 | Brown et al. |
| 3,133,578 A | 5/1964 | Moskovitz |
| 3,247,877 A | 4/1966 | Evans |
| 3,342,234 A | 9/1967 | Evans |
| 3,520,343 A | 7/1970 | Evans |
| 3,530,920 A | 9/1970 | Howard |
| 3,687,183 A | 8/1972 | Rohm |
| 3,701,372 A | 10/1972 | Breed |
| 3,721,283 A | 3/1973 | Evans |
| 3,731,725 A | 5/1973 | Brophy |
| 3,799,229 A | 3/1974 | Johnson |
| 3,882,917 A | 5/1975 | Orlomoski |
| 3,907,017 A | 9/1975 | Stanwick |
| 4,071,067 A | 1/1978 | Goldby |
| 4,076,064 A | 2/1978 | Holmes |
| 4,150,702 A | 4/1979 | Holmes |
| 4,171,012 A | 10/1979 | Holmes |
| 4,220,187 A | 9/1980 | Holmes |
| 4,351,626 A | 9/1982 | Holmes |
| 4,734,002 A | 3/1988 | Holmes |
| 4,826,377 A | 5/1989 | Holmes |
| 5,078,562 A | 1/1992 | Dehaitre |
| 5,242,252 A | 9/1993 | Haerle |
| 5,259,715 A | 11/1993 | Haerle |
| 5,738,472 A | 4/1998 | Roopnarine |
| 5,876,168 A | 3/1999 | Iwata |
| 6,558,423 B1 | 5/2003 | Michelson |
| 7,077,864 B2 | 7/2006 | Byrd et al. |
| 7,322,983 B2 | 1/2008 | Harris |
| 7,601,171 B2 * | 10/2009 | Ainsworth ............ A61B 17/025 623/17.11 |
| 7,740,633 B2 * | 6/2010 | Assell ................ A61B 17/8888 606/96 |
| 10,064,669 B2 * | 9/2018 | Garvey .............. A61B 17/8685 |
| 10,172,656 B1 * | 1/2019 | Reimels ............ A61B 17/8625 |
| 2003/0153919 A1 | 8/2003 | Harris |
| 2006/0276793 A1 | 12/2006 | Berry |
| 2008/0145178 A1 | 6/2008 | Curry |
| 2011/0106157 A1 | 5/2011 | Melkent et al. |
| 2011/0288598 A1 | 11/2011 | Moed et al. |
| 2012/0197311 A1 | 8/2012 | Kirschman |
| 2013/0096631 A1 | 4/2013 | Leung et al. |
| 2013/0211468 A1 | 8/2013 | Huebner |
| 2015/0105829 A1 | 4/2015 | Laird |
| 2016/0361096 A1 | 12/2016 | van der Pol |
| 2017/0042595 A1 | 2/2017 | Terrill et al. |
| 2018/0028236 A1 | 2/2018 | Ziemek et al. |
| 2018/0296261 A1 | 10/2018 | Kang et al. |

FOREIGN PATENT DOCUMENTS

| | | |
|---|---|---|
| EP | 2158863 A1 | 3/2010 |
| WO | 2011026644 A3 | 3/2011 |
| WO | 2013154437 A1 | 10/2013 |

OTHER PUBLICATIONS

International Search Report, Korean Intellectual Property Office, International application No. PCT/US2020/029676, mailed Aug. 5, 2020 (Aug. 5, 2020).

China Search Report. China National Intellectual Property Administration. 2 pgs.

CN106999288A-Google Patents English Translation.

CN107913098A-Google Patents English Translation.

* cited by examiner

RETENTION SYSTEM AND METHOD

CROSS REFERENCE TO RELATED APPLICATIONS

This application is a continuation of U.S. patent application Ser. No. 16/395,880, filed Apr. 26, 2019, which is expressly incorporated by reference herein, in its entirety.

TECHNICAL FIELD

The present disclosure generally relates to medical devices for the treatment of musculoskeletal disorders, and more particularly to a retention system including an implant and a screw that penetrates tissue and locks to the implant.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, such as, for example, bone fasteners, plates and interbody devices can be used to provide stability to a treated region. For example, during surgical treatment, interbody implants can be delivered to a surgical site for fixation with bone to immobilize a joint. The bone fasteners extend through a plate and/or an interbody device and into bone to fix at least a portion of the plate and/or the interbody device to the bone. This disclosure describes an improvement over these prior art technologies.

SUMMARY

In one embodiment, in accordance with the principles of the present disclosure, a retention system includes a first member comprising an inner surface defining a first thread form. The first thread form comprises a first stage having a first pitch and a second stage having a second pitch that is greater than the first pitch. A second member comprises a shaft and a neck. The shaft comprises an outer surface defining a second thread form configured to engage the first thread form to lock the second member with the first member. The neck comprises a smooth unthreaded section.

In one embodiment, in accordance with the principles of the present disclosure, a retention system includes a first member comprising an inner surface defining a first thread form. The first thread form comprises a single helix including a first stage having a first aperture cross-section and a second stage having a second aperture cross-section that is greater than the first aperture cross-section. A second member comprises a shaft and a neck. The shaft comprises an outer surface defining a second thread form configured to engage the female thread form to lock the second member with the first member. The neck comprises a smooth unthreaded section.

In one embodiment, in accordance with the principles of the present disclosure, a retention system includes a first member comprising a top surface, an opposite bottom surface and an inner surface defining a hole extending through the top and bottom surfaces. The inner surface further defines a first thread form. The first thread form comprises a first stage having a first pitch and a second stage having a second pitch that is greater than the first pitch. A second member comprises a head, a shaft and a neck positioned between the shaft and the head. An interface between the neck and the head defines a shoulder of the second member. The shaft comprises an outer surface defining a second thread form configured to engage the first thread form. The second thread form has a uniform pitch along an entire length of the second thread form. The neck comprises a smooth unthreaded first section and a second section comprising a plurality of teeth. The second member is unable to translate relative to the first member without rotating the second member relative to the first member when the second thread form is positioned within the first stage. The second member is able to translate relative to the first member without rotating the second member relative to the first member when the second thread form is positioned within the second stage and is spaced apart from the first stage. The shoulder is configured to engage the first thread form when the second thread form is positioned within the second stage and is spaced apart from the first stage such that engagement of the first thread form with the shoulder and rotation of the second member relative to the first member causes the second member to axially translate in a proximal direction relative to the first member. The second thread form engages the first thread form when the second member translates axially in the proximal direction relative to the first member to lock the second member with the first member. A last one of the teeth includes a relief that is configured to be wedged into a minor diameter of the first thread form when the second thread form is positioned within the second stage and is spaced apart from the first stage to lock the second member with the first member.

BRIEF DESCRIPTION OF THE DRAWINGS

The present disclosure will become more readily apparent from the specific description accompanied by the following drawings, in which.

DETAILED DESCRIPTION

Figure 1:
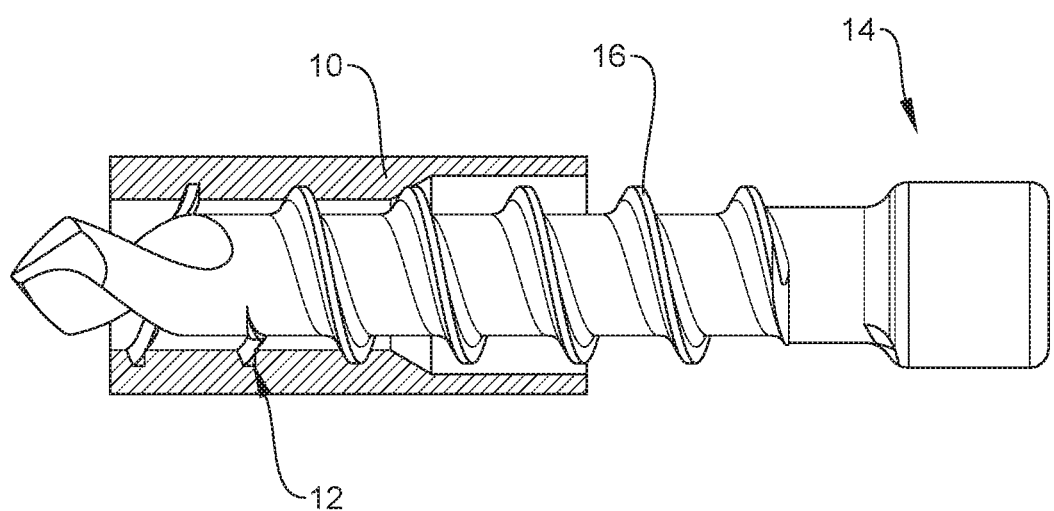
FIG. 1 is a side view of a first prior art retention mechanism.

The exemplary embodiments of the retention system and related methods of use disclosed are discussed in terms of medical devices for the treatment of musculoskeletal disorders and more particularly, in terms of a surgical retention system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present retention system is adapted to be used in various orthopedic procedures and/or with various medical devices that require a screw to penetrate bone and lock to implanted hardware. In one embodiment, the medical devices include interbody implants and plates, such as, for example, mini plates that are used throughout the thoracolumbar region of the spine.

In some embodiments, the present retention system includes a threaded bone screw retention mechanism for locking a bone screw to an implant using only the input torque of a driver to advance the screw, while allowing for gap reduction and desirable tactile feel. The present retention system includes an implant that includes a series of helical features on female threads. In one embodiment, a primary or first helical feature of the female threads matches male threads of the bone screw to allow the male threads to pass through. In some embodiments, the first helical feature includes a single start. In some embodiments, the primary helical feature includes multiple starts.

In some embodiments, a secondary or second helical feature of the female threads eliminates most of the implant material present between the crests of the pitch of the female thread. This cut follows a path that does not go all the way to a screw entry point of the implant and allows gaps to be reduced by letting the screw lag after a head of the bone screw is completely seated. In some embodiments, the implant includes a forward portion of material in front of the cut to ensure ease of removal of the screw. Without the forward portion of material, the screw will lag and perform the same. However, removal of the screw from the implant may be tedious because it would require manually pulling on the screw, while clocking it correctly to find the threads to return.

In one embodiment, a tertiary or third helical feature of the female threads follows a very shallow path only at the screw entry point of the implant that quickly tapers out to the minor diameter of the female threads. The surface of this feature is what engages a neck of the screw causing the screw to lock in a consistent and gradual manner. Without the third helical feature, the screw lock and lag will still function, but the tactile feel experienced by the user will be less consistent.

In some embodiments, the screw has teeth that are patterned radially around the neck before the head of the screw. The teeth are configured to provide variable lag. In one embodiment, the teeth include a tooth pattern that stops short at a last portion of material. This provides a final hard stop to engage after all the teeth have been acted on.

In some embodiments, the implant includes a female thread portion having female threads. The implant is shorter than a drill tip length of a screw such that bone can be engaged by the male threads of the screw just before the female threads of the body are engaged by the male threads of the screw. In some embodiments, the implant is long enough to provide angular guidance of the drill tip as it is pushed through to touch the bone.

In some embodiments, the male threads of the screw engage the female threads before the male threads engage the bone. As the screw is advanced into the implant, the male threads engage bone and set timing between the female thread portion and the bone. Any gap that is present is prevented from closing, even under load.

As the male threads engage bone, the first couple of teeth begin to strike a first surface of the implant and move on to a second surface of the implant. As the teeth engage the surfaces, the user may feel slight resistance. However, the screw can be rotated relative to the implant in a first rotational direction, such as, for example, clockwise, when such resistance is felt. As more teeth are engaged, resistance gradually increases. Before the head is fully seated, the last portion of the trailing flank of the male threads passes a third surface of the implant. The head stops advancing once the head bottoms out on a counterbore of the implant. Any gap that is left over is still present, but the screw can be rotated relative to the implant in the first rotational direction since there are still some male threads that have not engaged with any of the female threads.

The crests of the male threads are spun inside of a region of the implant to reduce the gap. In some embodiments, the amount the gap is reduced is equal to the pitch multiplied by the amount of extra rotation. In some embodiments, the screw can be overspun to close the gap until the last tooth of the screw comes into contact with the second surface of the implant and the user experiences a final hard stop. This protects the male threads from being stripped and limits the potential for the user to unknowingly core out the bone in the event that the screw is overspun without the presence of a gap.

Rotating the screw in an opposite second rotational direction, such as, for example, counter-clockwise results in the leading flank contacting the portion of forward material of the implant, which overcomes the lock and allows the screw to be removed from the implant. At this point, the screw is aligned with the female threads by which it entered, and is able to be removed.

In some embodiments, the present retention system allows the screw to close gaps between the male threads and the female threads within the implant or provide compression. In some embodiments, the present retention system allows the screw and/or the implant to have a low profile to enable improved inserter connection geometry. In some embodiments, the present retention system does not require any extra steps to lock the screw after driving the screw into bone. In some embodiments, the present retention system does not require assembly of components.

In some embodiments, the retention system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the retention system of the present disclosure may be employed with other osteal and bone related applications, including those associated with diagnostics and therapeutics. In some embodiments, the disclosed retention system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The retention system of the present disclosure may also be alternatively employed with procedures for treating the lumbar, cervical, thoracic, sacral and pelvic regions of a spinal column. The retention system of the present disclosure may also be used on animals, bone models and other non-living substrates, such as, for example, in training, testing and demonstration.

The retention system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a retention system including implants, related components and methods of employing the retention system in accordance with the principles of the present disclosure. Alternate embodiments are also disclosed. Reference is made in detail to the exemplary embodiments of a retention system 20, which are illustrated in the accompanying figures.

The components of retention system 20 can be fabricated from biologically acceptable materials suitable for medical applications, including metals, synthetic polymers, ceramics and bone material and/or their composites. For example, the components of retention system 20, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of retention system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of retention system 20 may be monolithically formed, integrally connected or include fastening elements and/or instruments, as described herein.

Retention system 20 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 2:
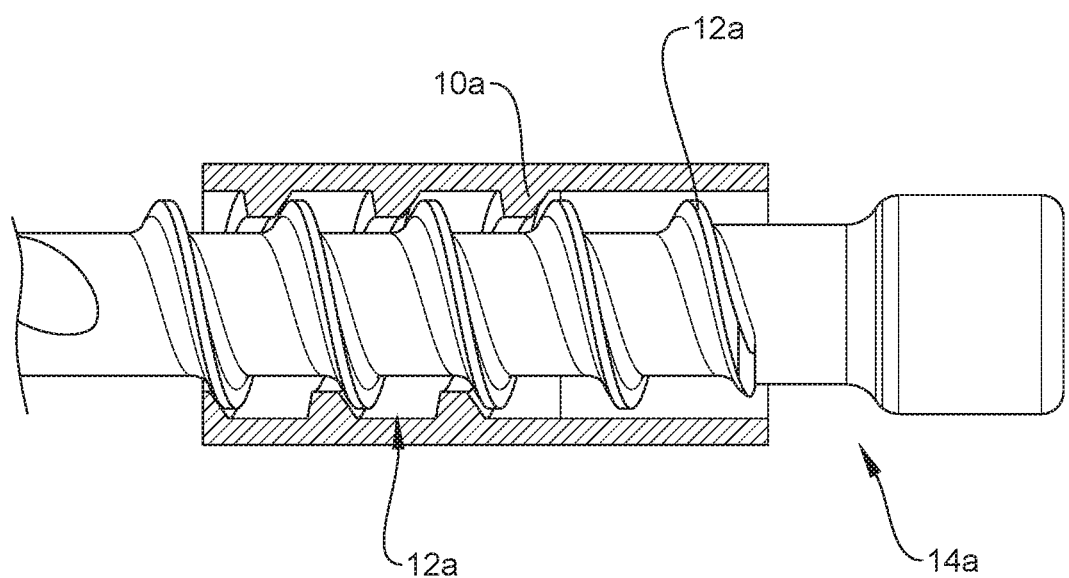
FIG. 2 is a side view of a second prior art retention mechanism.

As shown in FIG. 1, prior art fastening systems may include a body 10 defining a female thread form 12 and a screw 14 defining a male thread form 16 wherein the pitch of female thread form 12 is the same as the pitch of male thread form 16. As such, screw 14 is unable to translate relative to body 10 without rotating screw 14 relative to body 10. As shown in FIG. 2, prior art fastening systems may include a body 10a defining a female thread form 12a and a screw 14a defining a male thread form 16a wherein the pitch of female thread form 12a is greater than the pitch of male thread form 16a. As such, screw 14a able to translate relative to body 10a without rotating screw 14a relative to body 10a. Heretofore unknown is a retention system wherein a screw is unable to translate relative to a body without rotating the screw relative to the body when a male thread form of the screw engages a first portion of a female thread of the body and is able to translate relative to the body without rotating the screw relative to the body when the male thread form of the screw engages a second portion of the female thread of the body to lock the screw with the body. This disclosure describes an improvement over these prior art technologies.

Figure 3:
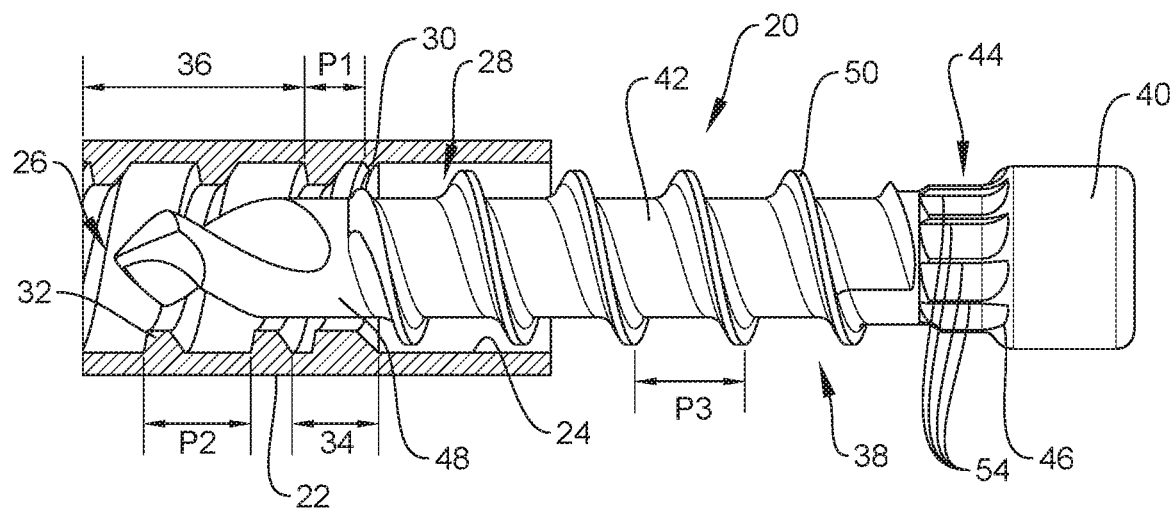
FIG. 3 is a side view, in part cross-section, of a retention system, in accordance with the principles of the present disclosure.
Figure 4:
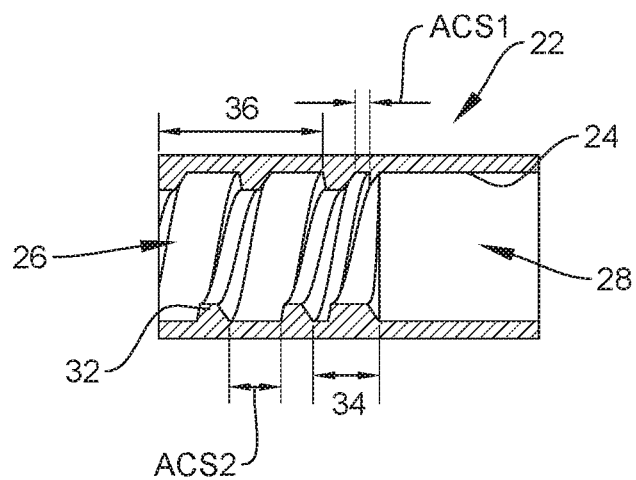
FIG. 4 is a side, cross-sectional view of a component of the system shown in FIG. 3.
Figure 5:
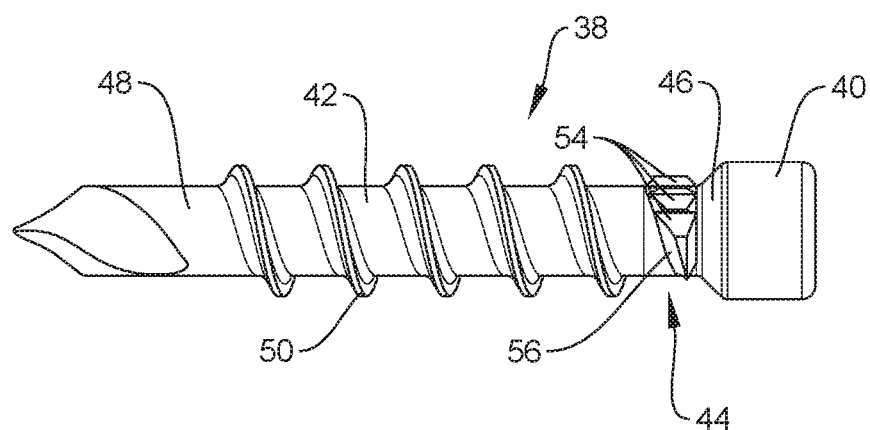
FIG. 5 is a side view of a component of the system shown in FIG. 3.
Figure 6:
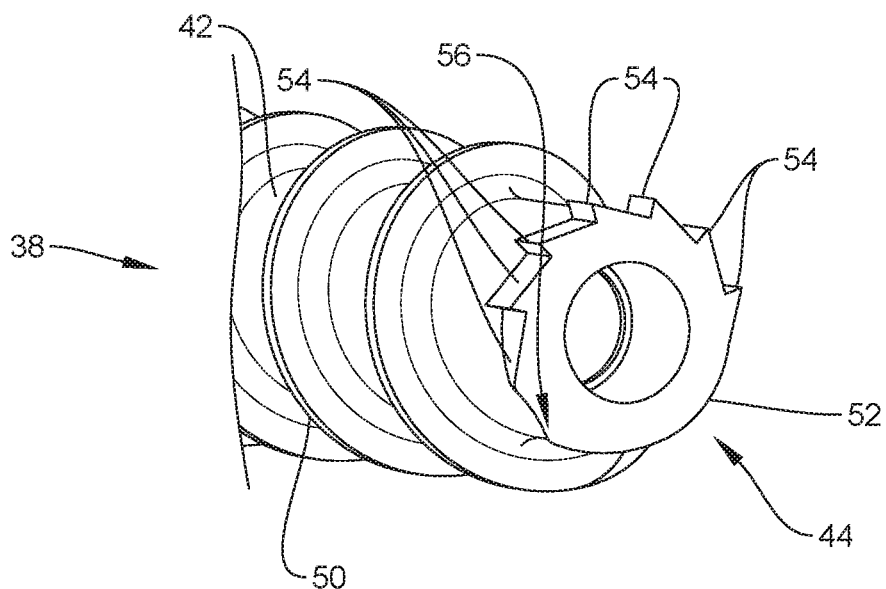
FIG. 6 is a perspective, cross-sectional view of a component of the system shown in FIG. 3.

In one embodiment, shown in FIGS. 3-9, retention system 20 includes a first member, such as, for example, a body 22 comprising an inner surface 24 defining a bore 26 and a counterbore 28. Counterbore 28 is separated from bore 26 by a shoulder 30. Surface 24 further defines a first thread form, such as, for example, a helical female thread form 32, as shown in FIGS. 3 and 4, for example. Thread form 32 includes a first stage 34 and a second stage 36. Stage 34 has a first pitch P1 and stage 36 has second pitch P2 that is greater than first pitch P1. Stated another way, stage 34 has an aperture cross-section ACS1 that is less than an aperture cross-section ACS2 of stage 36, as shown in FIG. 4, for example. Thread form 30 thus is a singular helix of varying aperture cross-section. In some embodiments, body 22 is part of an implant, such as, for example, a spinal implant configured to be implanted within a body of a patient. In some embodiments, first pitch P1 is defined by the distance from a first crest of stage 34 to an adjacent crest of stage 34 and second pitch P2 is defined by the distance from a first crest of stage 36 to an adjacent crest of stage 36.

Figure 15:
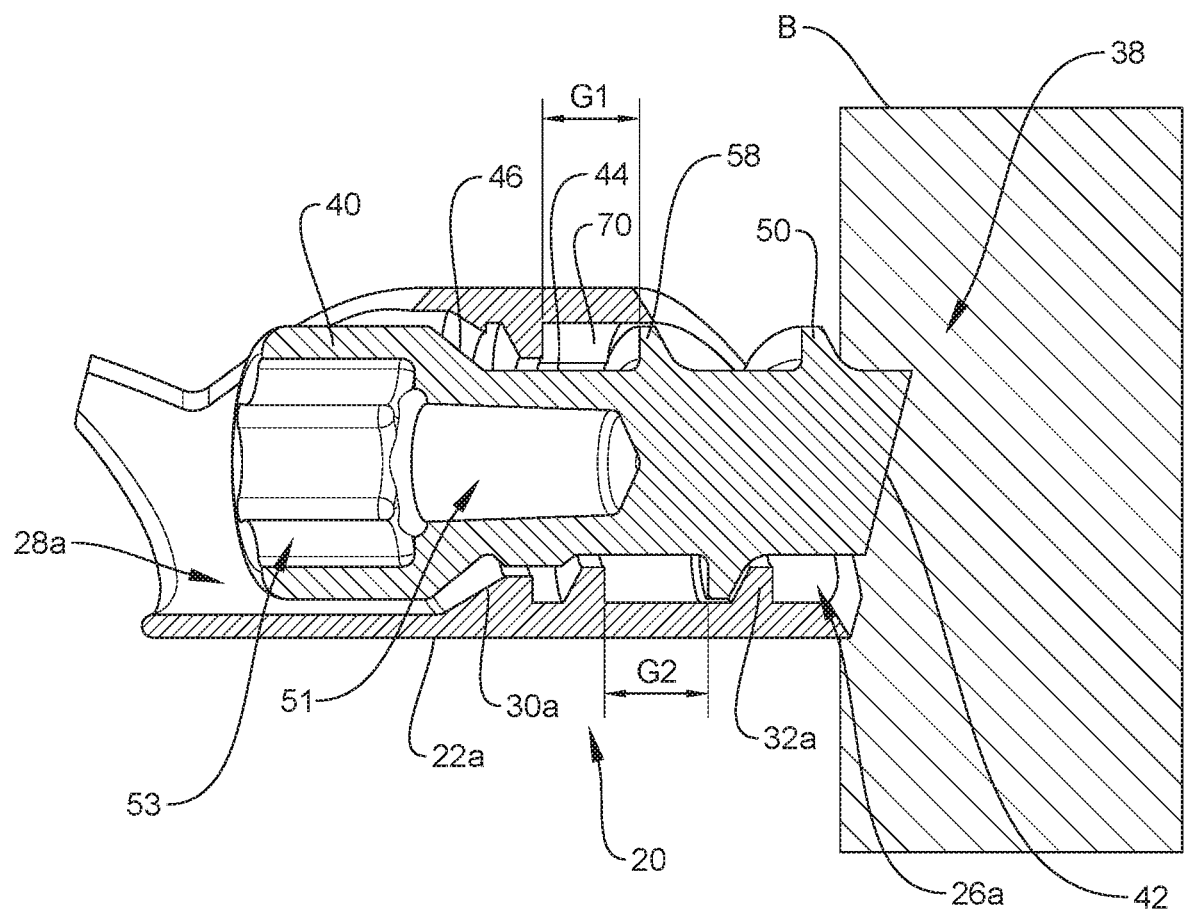
FIG. 15 is a side view, in part cross-section, of components of the retention system shown in FIG. 10.

Retention system 20 includes a second member, such as, for example, a screw 38 comprising a head 40, a shaft 42 and a neck 44 positioned between head 40 and shaft 42. An interface between neck 44 and head 40 defines a shoulder 46. Shaft 42 comprises an outer surface 48 defining a second thread form, such as, for example, a male thread form 50 configured to engage female thread form 32 to lock the screw 38 with body 22. In some embodiments, male thread form 50 has a constant pitch P3 along the entire length of male thread form 50. That is, unlike thread form 32, thread form 500 is a singular helix having a consistent aperture cross-section. Neck 44 comprises a first portion including a smooth unthreaded section 52 (FIG. 7) configured to allow screw 38 to translate relative to body 22 when male thread form 50 engages female thread form 32, as discussed herein. In some embodiments, screw 38 includes a bore 51 that extends through neck 44 and into shaft 42, as shown in FIG. 15, for example. Screw 38 further includes a socket 53 positioned in head 40 such that bore 51 is positioned between socket 53 and a distal tip of shaft 42. Socket 53 includes a hexalobe cross-sectional configuration configured for engagement with a bit of a driver having a hexalobe cross-sectional configuration to rotate screw 38. However, it is envisioned that socket 53 may include a square, triangular, polygonal, star cross sectional configuration configured engage a correspondingly shaped bit of a driver. In some embodiments, pitch P3 is defined by the distance from a first crest of male thread form 50 to an adjacent crest of male thread form 50.

Figure 7:
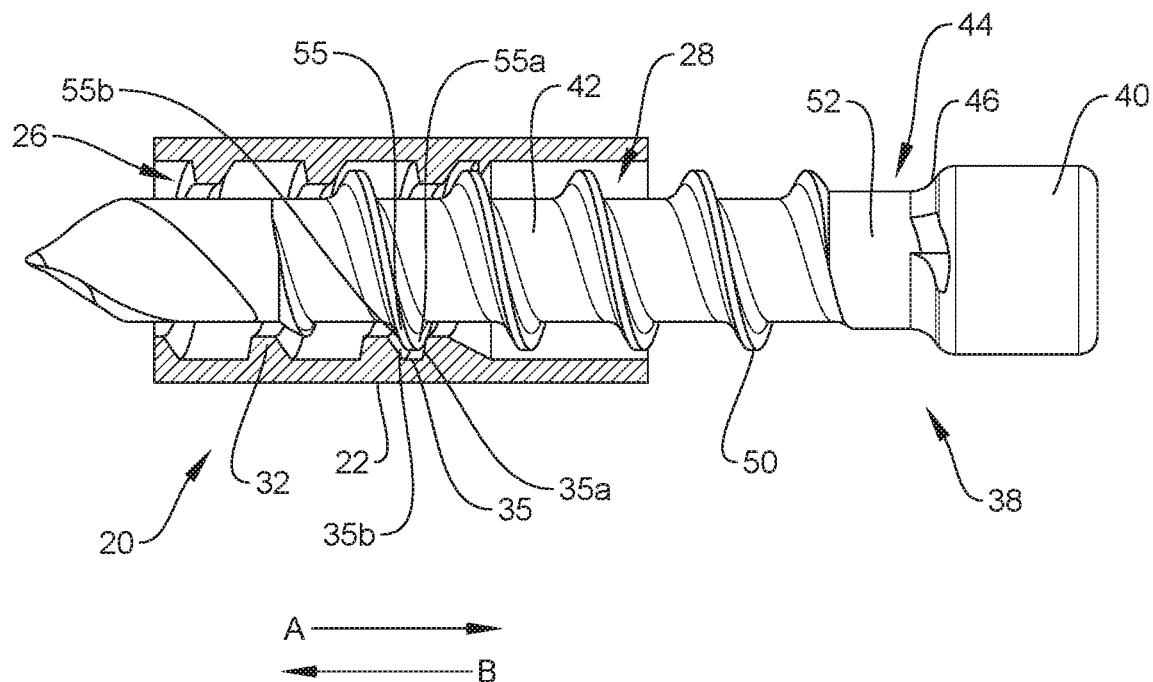
FIG. 7 is a side view, in part cross-section, of components of the system shown in FIG. 3.

Screw 38 is configured to be inserted through counterbore 28 and into bore 26 such that male thread form 50 is positioned within first stage 34, as shown in FIG. 7. A trailing edge 55a of a crest 55 of thread form 50 engages an upper edge 35a of a root 35 of thread form 32 and a leading edge 55b of crest 55 engages a lower edge 35b of root 35 such that screw 38 is prevented from translating relative to body 22 in the direction shown by arrow A in FIG. 7 or the direction shown by arrow B in FIG. 7 without rotating screw 38 relative to body 22. That is, crest 55 is prevented from moving axially within root 35 to prevent screw 38 translating relative to body 22 in the direction shown by arrow A in FIG. 7 or the direction shown by arrow B in FIG. 7 without rotating screw 38 relative to body 22.

Figure 8:
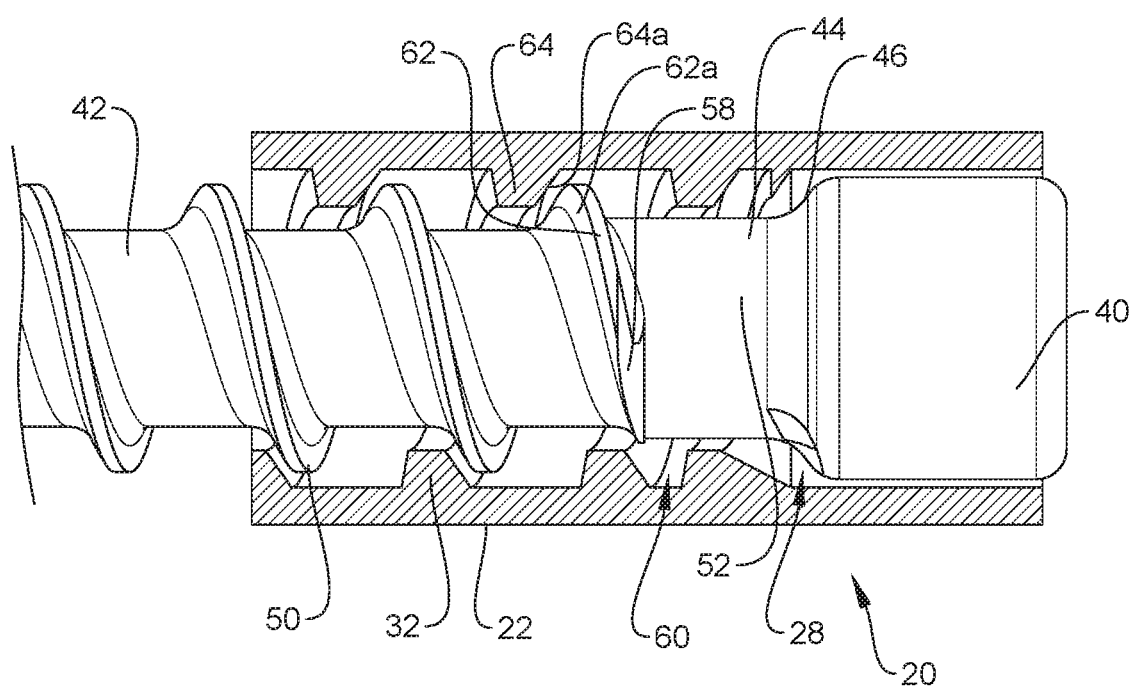
FIG. 8 is a side view, in part cross-section, of components of the system shown in FIG. 3.

Screw 38 is rotated in a first rotational direction, such as, for example, clockwise to translate screw 38 relative to body 22 in the direction shown by arrow B in FIG. 7. In particular, screw 38 is rotated in the first rotational direction to translate screw 38 relative to body 22 in the direction shown by arrow B in FIG. 7 until a trailing flank 58 of male thread form 50 passes a gate 60 of female thread form 32, as shown in FIG. 8. When trailing flank 58 passes gate 60, a portion of male thread form 50 is positioned within second stage 36, as shown in FIG. 8. When trailing flank 58 passes gate 60, a leading edge 62a of a proximal crest 62 of male thread form 50 engages an upper edge 64a of a crest 64 of female thread form 32 such that screw 38 is able to translate and/or lag relative to body 22 in the direction shown by arrow A in FIG. 7.

Figure 9:
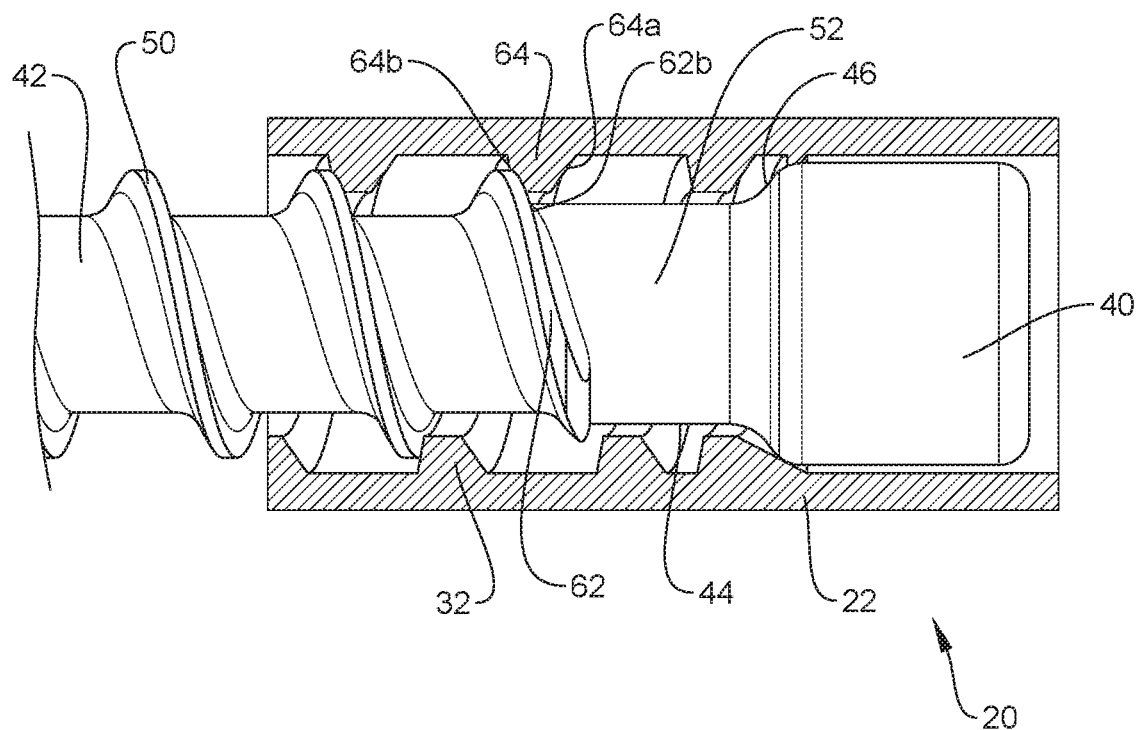
FIG. 9 is a side view, in part cross-section, of components of the system shown in FIG. 3.

Screw 38 is further rotated in the first rotational direction to translate screw 38 relative to body 22 in the direction shown by arrow B in FIG. 7 until a trailing edge 62b of crest 62 engages an upper edge 64b of crest 64, as shown in FIG. 9, to lock screw 38 relative to body 22. Once trailing edge 62b of crest 62 engages upper edge 64b of crest 64, further rotation of screw 38 in the first rotational direction will not translate screw 38 relative to body 22 in the direction shown by arrow B in FIG. 7. Rather, once trailing edge 62b of crest 62 engages upper edge 64b of crest 64, further rotation of screw 38 in the first rotational direction will translate screw 38 relative to body 22 in the direction shown by arrow A in FIG. 7 to lock screw 38 relative to body 22. In the embodiment shown in FIGS. 3-9, locking screw 38 relative to body 22 is entirely dependent on pitches P1, P2 of female thread form 32 and pitch P3 of male thread form 50.

In assembly, operation and use, retention system 20, similar to the systems and methods described herein, is employed with a surgical procedure for treatment of a spinal disorder affecting a section of a spine of a patient, as discussed herein. The components of retention system 20 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, retention system 20 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument creates a surgical pathway for implantation of components of retention system 20. A preparation instrument can be employed to prepare tissue surfaces of vertebrae as well as for aspiration and irrigation of a surgical region. A pilot hole is made in a vertebra for receiving shaft 42. Body 22 is positioned over the pilot hole such that bore 26 is coaxial with the pilot hole. Shaft 42 is positioned in the pilot hole and is rotated relative to the vertebra using a driver, for example, such that thread form 50 directly engages tissue to drive shaft 42 into to the tissue. In some embodiments, thread form 50 directly engages tissue before thread form 50 engages thread form 32. Further rotation of screw 38 causes thread form 50 to engage thread form 32. Thread form 50 engages tissue and sets the timing between the device and the tissue. Screw 38 is further rotated in the first rotational direction to translate screw 38 relative to body 22 in the direction shown by arrow B in FIG. 7 until a trailing edge 62*b* of crest 62 engages an upper edge 64*b* of crest 64, as shown in FIG. 9, to lock screw 38 relative to body 22.

In one embodiment, shown in FIGS. 10-19, system 20 is configured to provide a wedging effect between a screw, such as, screw 38 and a body 22*a* that is similar to body 22, wherein the wedging effect acts as a final lock, as discussed herein. That is, the embodiment shown in FIGS. 10-19 does not rely solely upon pitches P1, P2 of female thread form 32 and pitch P3 of male thread form 50 to lock screw 38 relative to body 22*a*. Rather, the embodiment shown in FIGS. 10-19 relies upon pitches P1, P2 of female thread form 32 and pitch P3 of male thread form 50 to provisionally lock screw 38 with body 22*a*, and then relies upon a wedging effect between screw 38 and body 22*a* to act as a final lock between screw 38 and body 22*a*.

Body 22*a* includes an inner surface 24 defining a bore 26*a* and a counterbore 28*a*. Counterbore 28*a* is separated from bore 26*a* by a shoulder 30*a*. Surface 24*a* further defines a first thread form, such as, for example, a helical female thread form 32*a*. Thread form 32*a* includes a first stage 34*a* and a second stage 36*a*. Stage 34*a* has a pitch P4 and stage 36*a* has pitch P5 that is greater than first pitch P4. Stated another way, stage 34*a* has an aperture cross-section ACS1*a* that is less than an aperture cross-section ACS2*a* of stage 36*a*, as shown in FIG. 4, for example. Thread form 30*a* thus is a singular helix of varying aperture cross-section. In some embodiments, body 22*a* is part of an implant, such as, for example, a spinal implant configured to be implanted within a body of a patient.

Neck 44 further comprises a second portion including a plurality of teeth 54 configured for engagement with surface 24*a* to lock screw 38 with body 22*a*, as discussed herein. In such embodiments, neck 44 further comprises a linear portion 56 that provides a final hard stop to engage screw 38 with body 22*a* after all of teeth 54 have been acted on, as discussed herein.

Figure 10:
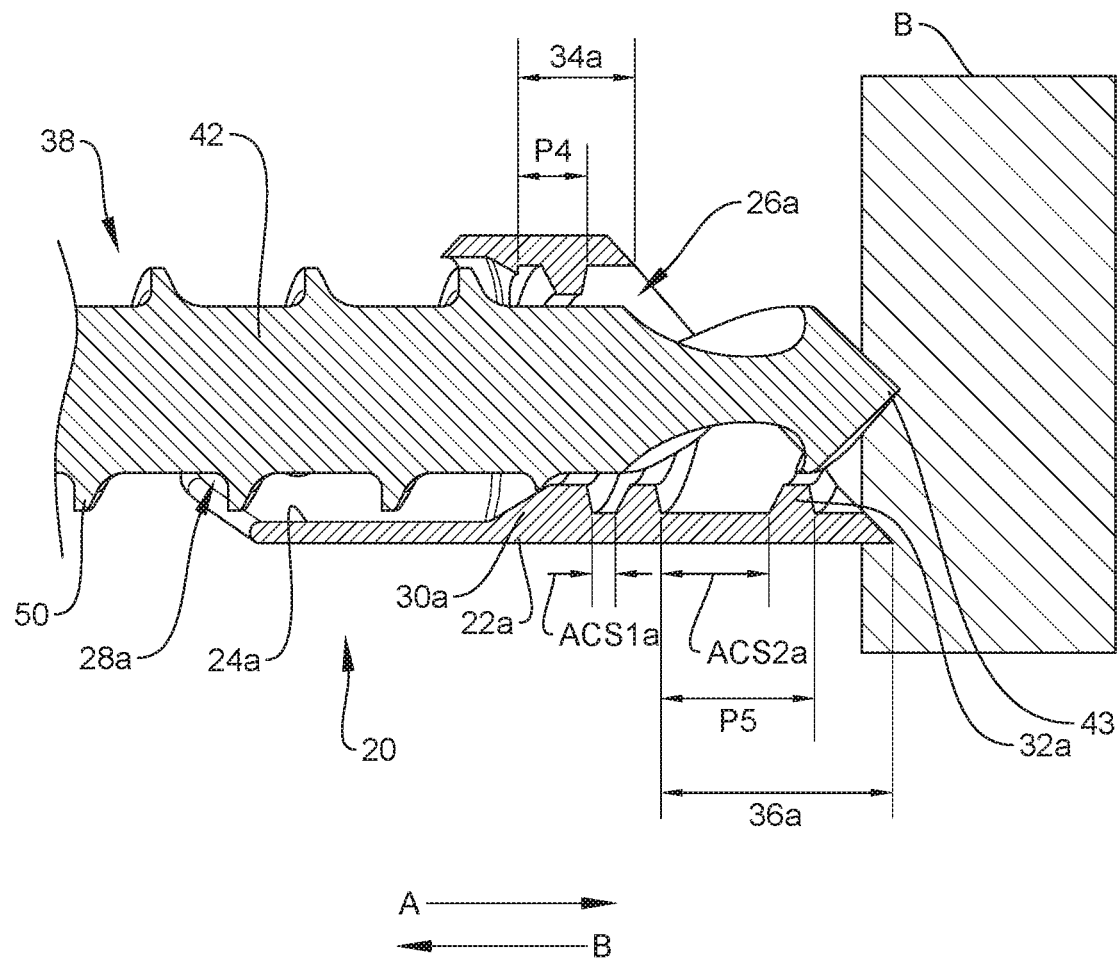
FIG. 10 is a side, cross-sectional view of a retention system, in accordance with the principles of the present disclosure.
Figure 11:
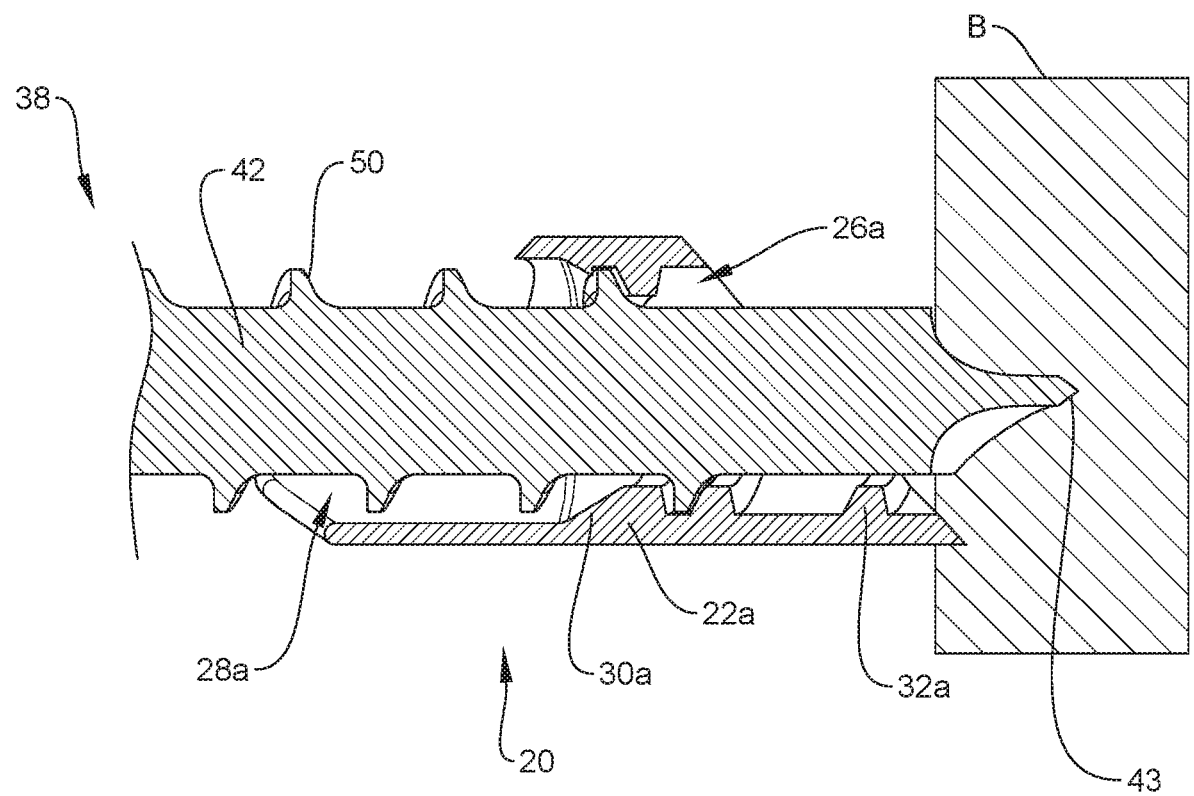
FIG. 11 is a side, cross-sectional view of components of the retention system shown in FIG. 10.

In some embodiments, the length of shaft 42 is greater than the length of body 22*a* such that a tip 43 of shaft 42 can engage tissue, such as, for example, bone B, before thread 50 engages thread 32*a*, as shown in FIG. 10. This allows a user to provide angular guidance of tip 43 as tip 43 is pushed through to touch bone B. Screw 38 is rotated relative to body 22*a* in the first rotational direction to translate screw 38 relative to body 22*a* in the direction shown by arrow A in FIG. 10 until thread form 50 engages thread form 32*a*, as shown in FIG. 11. As shown in FIG. 11, thread form 50 engages thread form 32*a* before thread from 50 engages bone B.

Figure 12:
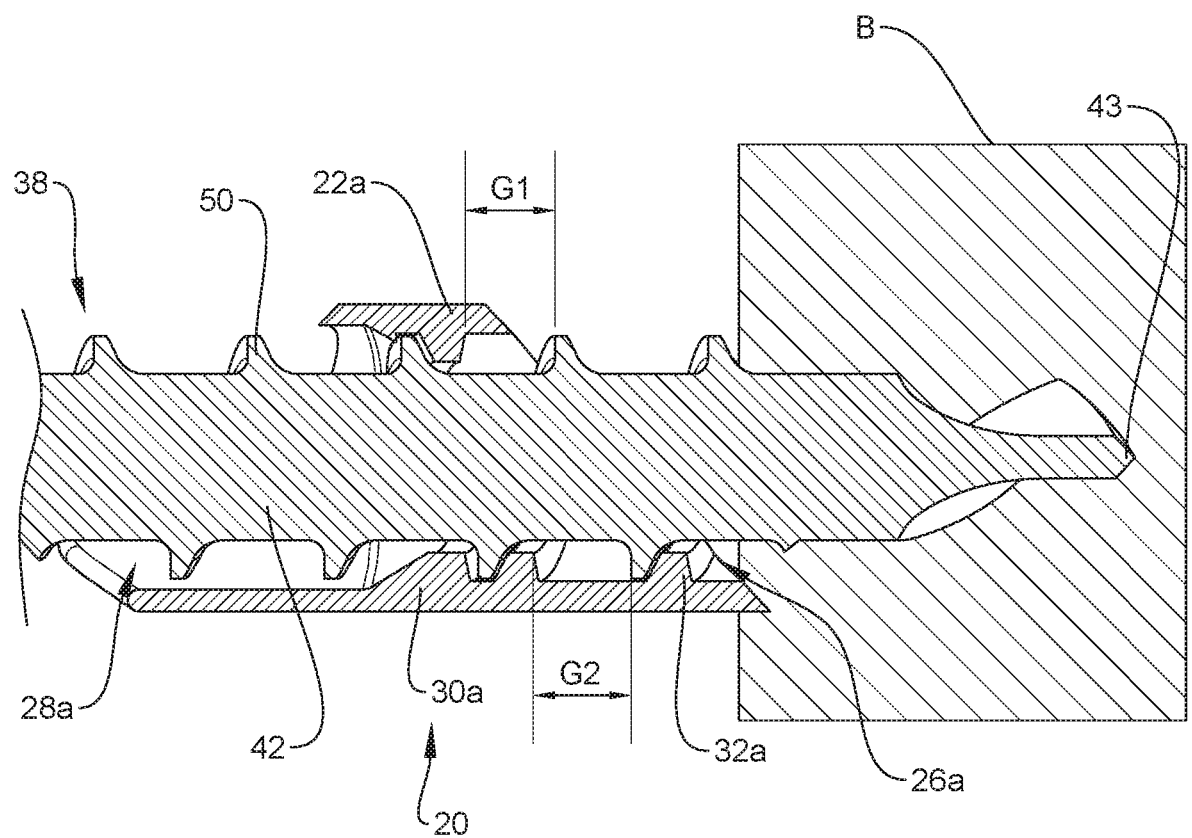
FIG. 12 is a side, cross-sectional view of components of the retention system shown in FIG. 10.

Screw 38 is further is rotated relative to body 22*a* in the first rotational direction to further translate screw 38 relative to body 22*a* in the direction shown by arrow A in FIG. 10 such that thread form 50 engages bone B, as shown in FIG. 12, to set the timing between screw 38 and bone B. At this point, any gap that is present between thread form 50 and thread form 32*a*, such as, for example, gap G1 and/or gap G2 shown in FIG. 12, is prevented from closing, even under load.

Figure 13:
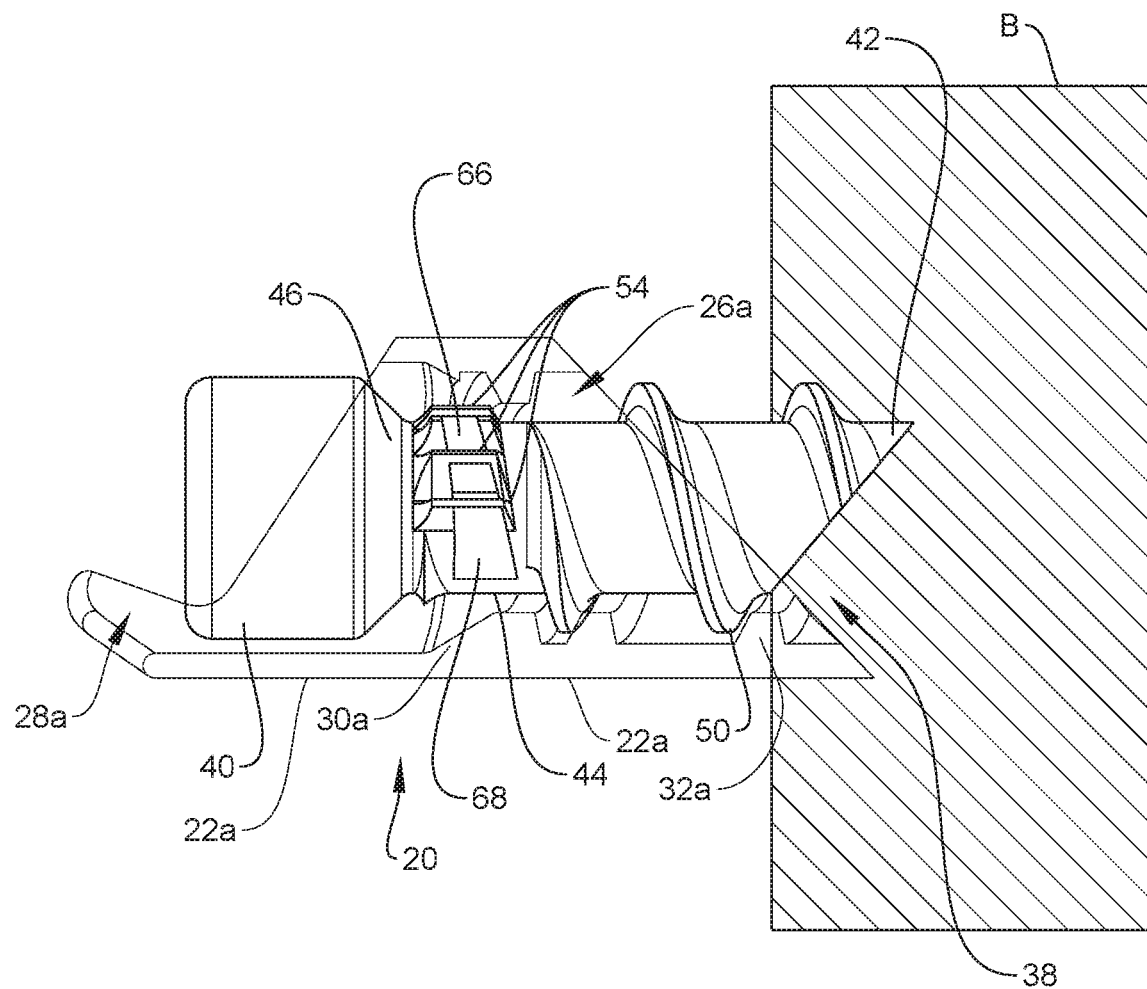
FIG. 13 is a side view, in part phantom, of components of the retention system shown in FIG. 10.
Figure 14:
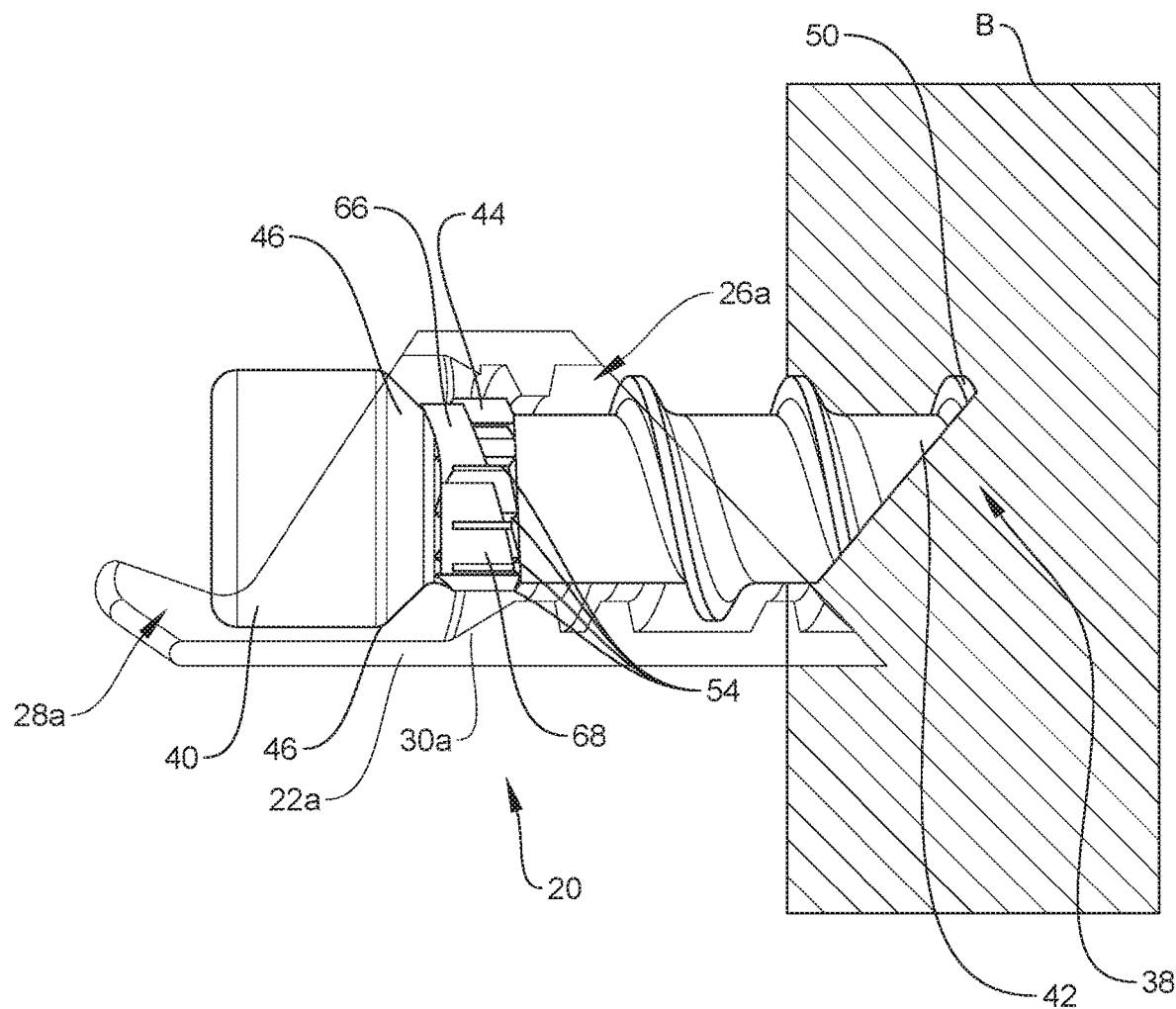
FIG. 14 is a side view, in part phantom, of components of the retention system shown in FIG. 10.

Screw 38 is further is rotated relative to body 22*a* in the first rotational direction to further translate screw 38 relative to body 22*a* in the direction shown by arrow A in FIG. 10 such that at least one of teeth 54 strike a surface 66 of body 20*a*, as shown in FIG. 13. Screw 38 further is rotated relative to body 22*a* in the first rotational direction such that at least one of teeth 54 strike a surface 68 of body 20*a*. As of teeth 54 strike surface 68 the user may feel a slight resistance. However, screw 38 can be further is rotated in the first rotational direction. As more teeth 54 engage surface 66 and/or surface 68, as shown in FIG. 14, resistance gradually increases.

Figure 16:
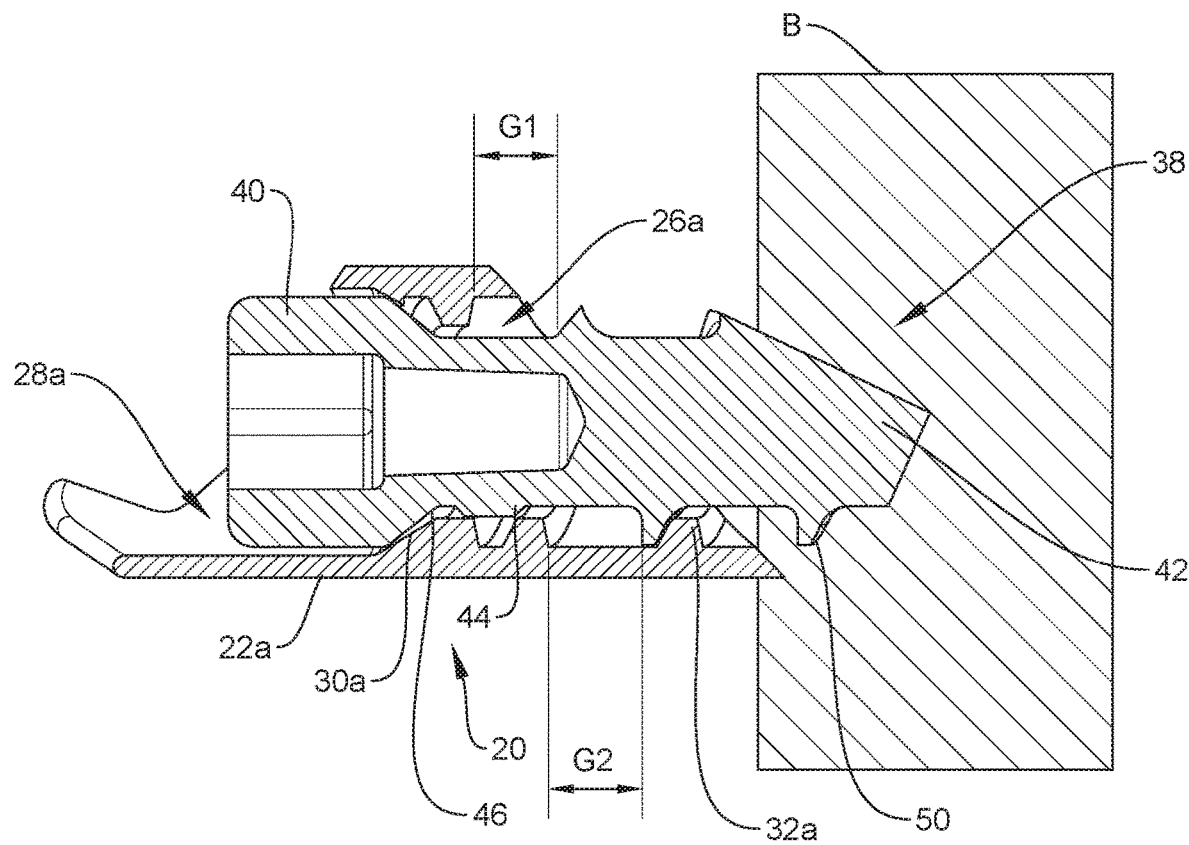
FIG. 16 is a side, cross-sectional view of components of the retention system shown in FIG. 10.

Before head 40 is fully seated in counterbore 28*a* such that shoulder 46 of screw 38 engages shoulder 30*a* of body 22*a*, trailing flank 58 passes a surface 70 of body 22*a*, as shown in FIG. 15. Screw 38 further is rotated relative to body 22*a* in the first rotational direction to further translate screw 38 relative to body 22*a* in the direction shown by arrow A in FIG. 10 such that shoulder 46 of screw 38 engages shoulder 30*a* of body 22*a*, as shown in FIG. 16. When shoulder 46 of screw 38 engages shoulder 30*a* of body 22*a* gaps between thread form 50 and thread form 32*a*, such as, for example, gaps G1, G2 remain. However, since at least one of teeth 54 has not yet engaged surface 66 and/or surface 68, screw 38 can be further rotated relative to body 22*a* in the first rotational direction.

Figure 17:
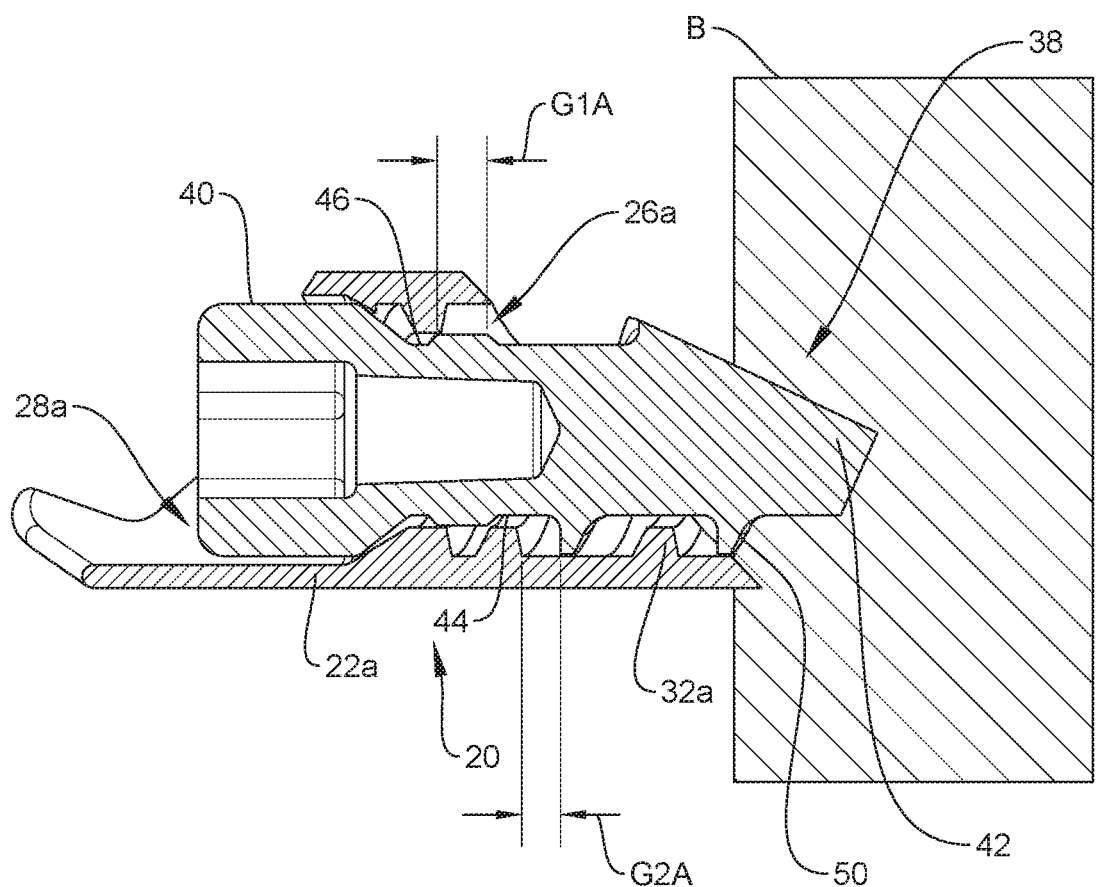
FIG. 17 is a side, cross-sectional view of components of the retention system shown in FIG. 10.

Screw 38 is further is rotated relative to body 22*a* in the first rotational direction such that threads of thread form 50 spin within gaps G1, G2. As threads of thread form 50 spin within gaps G1, G2, screw 38 translates relative to body 22*a* in the direction shown by arrow B in FIG. 10 to reduce gap G1 to a gap G1A and to reduce gap G2 to a gap G2A, as shown in FIG. 17. In some embodiments, the amount gap G1 is reduced to gap G1A and/or the amount gap G2 is reduced to gap G2 is equal to pitch P4 multiplied by the amount of extra rotation of screw 38 relative to body 22*a*.

Figure 18:
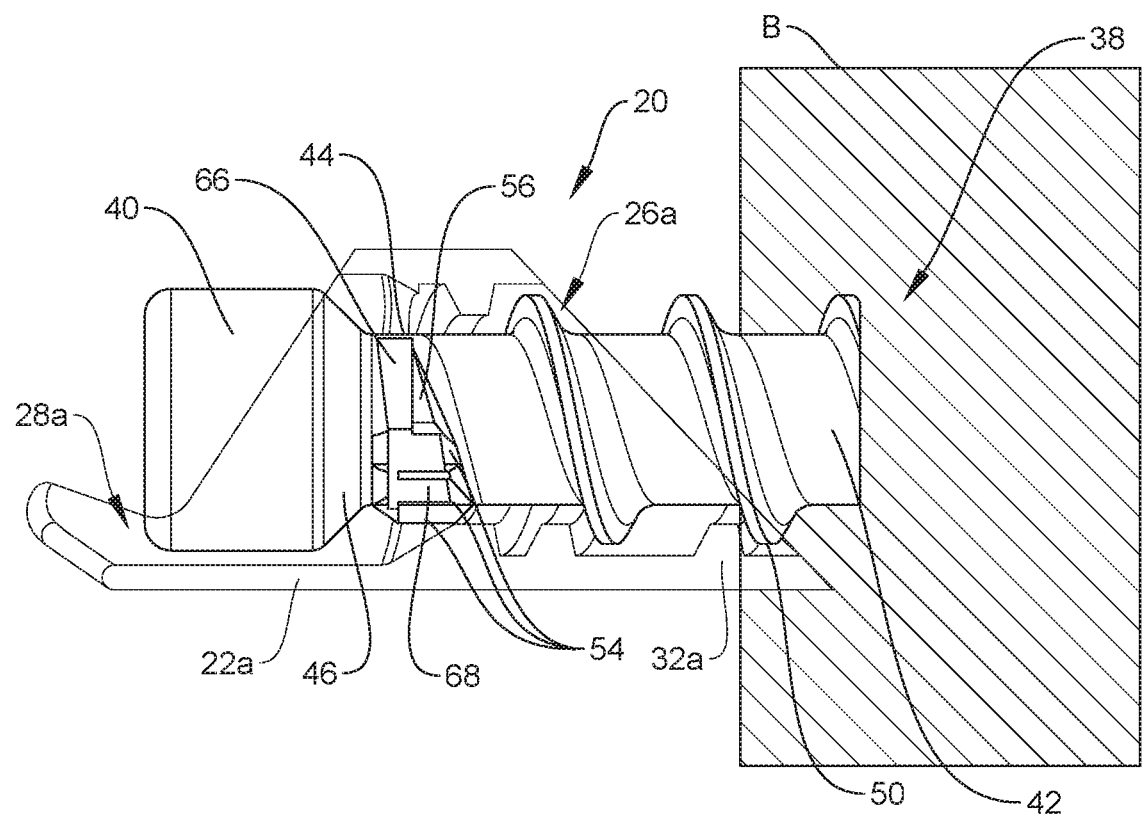
FIG. 18 side view, in part phantom, of components of the retention system shown in FIG. 10.

Screw 38 is further is rotated relative to body 22*a* in the first rotational direction to close any gaps between thread form 50 and thread form 32*a*, such as, for example, gaps G1A, G2A, as shown in FIG. 18. In particular, as screw 38 is further is rotated relative to body 22*a* in the first rotational direction, linear portion 56 engages surface 68 such that the user experiences a final hard stop. This protects thread form 50 and/or thread form 32a from being stripped and limits the potential for the user to unknowingly core out bone B in the event screw 38 is overspun without the presence of a gap between thread form 50 and thread form 32a.

Figure 19:
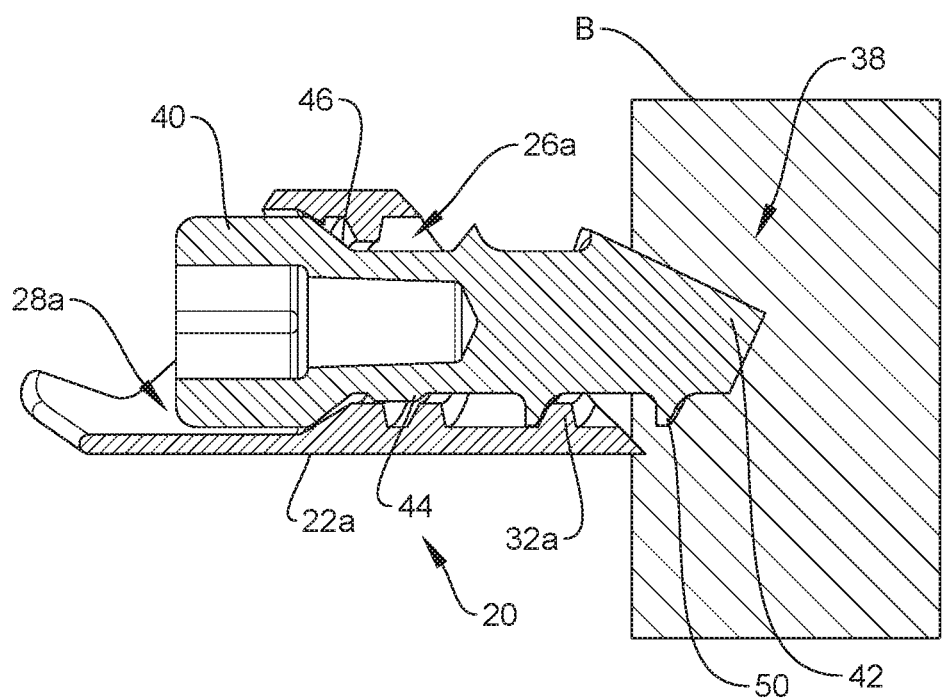
FIG. 19 is a side, cross-sectional view of components of the retention system shown in FIG. 10.

To remove screw 38 from body 22a, screw 38 is rotated relative to body 22a in a second rotational direction, such as, for example, counterclockwise such that screw 38 translates relative to body 22a in the direction shown by arrow B in FIG. 10. As screw 38 translates relative to body 22a in the direction shown by arrow B in FIG. 10, a leading flank 72 of thread form 50 engages an upper surface 74 of a thread of thread form 32a, as shown in FIG. 19, which aligns thread form 50 with thread form 32a, such that thread form 50 is positioned in the stage 36a. Screw 38 is fully removed from body 22a by further rotating screw 38 relative to body 22a in a second rotational direction.

In assembly, operation and use, retention system 20, similar to the systems and methods described herein, is employed with a surgical procedure for treatment of a spinal disorder affecting a section of a spine of a patient, as discussed herein. The components of retention system 20 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, retention system 20 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument creates a surgical pathway for implantation of components of retention system 20. A preparation instrument can be employed to prepare tissue surfaces of vertebrae as well as for aspiration and irrigation of a surgical region. A pilot hole is made in a vertebra for receiving shaft 42. Body 22a is positioned over the pilot hole such that bore 26a is coaxial with the pilot hole. Shaft 42 is positioned in the pilot hole and is rotated relative to the vertebra using a driver, for example, such that thread form 50 directly engages tissue to drive shaft 42 into to the tissue. In some embodiments, thread form 50 directly engages tissue before thread form 50 engages thread form 32a. Further rotation of screw 38 causes thread form 50 to engage thread form 32a. Thread form 50 engages tissue and sets the timing between the device and the tissue. Screw 38 is further rotated in the first rotational direction to translate screw 38 relative to body 22a in the direction shown by arrow B in FIG. 10 until any gaps between thread form 50 and thread form 32a, such as, for example, gaps G1A, G2A are closed to lock screw 38 with body 22a.

Upon completion of a procedure, as described herein, the surgical instruments, assemblies and non-implanted components of retention system 20 are removed and the incision(s) are closed. One or more of the components of retention system 20 can be made of radiolucent materials such as polymers. Radiomarkers may be included for identification under x-ray, fluoroscopy, CT or other imaging techniques. In some embodiments, retention system 20 may include one or a plurality of spinal rods, plates, connectors and/or bone fasteners for use with a single vertebral level or a plurality of vertebral levels.

In some embodiments, one or more bone screws, as described herein, may be engaged with tissue in various orientations, such as, for example, series, parallel, offset, staggered and/or alternate vertebral levels. In some embodiments, one or more of the bone screws may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, retention system 20 includes an agent, which may be disposed, packed, coated or layered within, on or about the components and/or surfaces of retention system 20. In some embodiments, the agent may include bone growth promoting material, such as, for example, bone graft to enhance fixation of the components and/or surfaces of retention system 20 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A retention system comprising:
 a first member comprising an inner surface defining a first thread, the first thread comprising a first stage having a first pitch and a second stage having a second pitch that is greater than the first pitch; and
 a second member comprising a shaft, the shaft defining a second thread having a third pitch,
 wherein the second thread is configured to be threaded with the first thread such that the pitches cause the second member to provisionally lock with the first member and a wedging effect between the second member and the first member acts as a final lock between the second member and the first member, and
 wherein the second member is able to translate relative to the first member without rotating the second member relative to the first member when the second thread is positioned within the second stage and is spaced apart from the first stage.

2. The retention system recited in claim 1, wherein the second member comprises a head and a neck positioned between the shaft and the head, the neck comprising a plurality of teeth.

3. The retention system recited in claim 2, wherein at least one of the teeth is configured to engage the first thread when the second thread is positioned within the second stage and is spaced apart from the first stage to define the final lock.

4. The retention system recited in claim 2, wherein at least one of the teeth includes a relief that is configured to be wedged into a minor diameter of the first thread when the second thread is positioned within the second stage and is spaced apart from the first stage to define the final lock.

5. The retention system recited in claim 2, wherein neck includes a linear portion that provides a final hard stop to engage the second member with the first member after all of the teeth have acted on the first member.

6. The retention system recited in claim 1, wherein the second member comprises a head and a neck positioned between the shaft and the head, an interface between the neck and the head defining a shoulder, the shoulder being configured to engage the first thread when the second thread is positioned within the second stage and is spaced apart from the first stage such that engagement of the first thread with the shoulder and rotation of the second member relative to the first member causes a trailing edge of the second thread to engage the first thread.

7. The retention system recited in claim 1, wherein the first thread comprises a single helix.

8. The retention system recited in claim 1, wherein the second thread has a uniform pitch along an entire length of the second thread.

9. The retention system recited in claim 1, wherein a maximum length of the shaft is greater than a maximum length of the first member.

10. A retention system comprising:
a spinal implant comprising an inner surface defining a first thread, the first thread comprising a first stage having a first pitch and a second stage having a second pitch that is greater than the first pitch; and
a screw comprising a shaft, the shaft defining a second thread having a third pitch,
wherein the second thread is configured to be threaded with the first thread such that the pitches cause the screw to provisionally lock with the implant and a wedging effect between the screw and the implant acts as a final lock between the screw and the implant, and
wherein the screw is able to translate relative to the spinal implant without rotating the screw relative to the spinal implant when the second thread is positioned within the second stage and is spaced apart from the first stage.

11. The retention system recited in claim 10, wherein the screw is able to translate relative to the implant without rotating the screw relative to the implant when the second thread is positioned within the second stage and is spaced apart from the first stage.

12. The retention system recited in claim 10, wherein the screw comprises a head and a neck positioned between the shaft and the head, the neck comprising a plurality of teeth.

13. The retention system recited in claim 12, wherein at least one of the teeth is configured to engage the first thread when the second thread is positioned within the second stage and is spaced apart from the first stage to define the final lock.

14. The retention system recited in claim 12, wherein at least one of the teeth includes a relief that is configured to be wedged into a minor diameter of the first thread when the second thread is positioned within the second stage and is spaced apart from the first stage to define the final lock.

15. The retention system recited in claim 12, wherein neck includes a linear portion that provides a final hard stop to engage the screw with the implant after all of the teeth have acted on the implant.

16. The retention system recited in claim 10, wherein the screw comprises a head and a neck positioned between the shaft and the head, an interface between the neck and the head defining a shoulder, the shoulder being configured to engage the first thread when the second thread is positioned within the second stage and is spaced apart from the first stage such that engagement of the first thread with the shoulder and rotation of the screw relative to the implant causes a trailing edge of the second thread to engage the first thread.

17. The retention system recited in claim 10, wherein the third pitch is equal to the first pitch.

18. The retention system recited in claim 10, wherein the third pitch is less than the second pitch.

19. A retention system for an implant, the locking system comprising:
a first member comprising a top surface, an opposite bottom surface and an inner surface defining a hole extending through the top and bottom surfaces, the inner surface further defining a first thread, the first thread comprising a first stage having a first pitch and a second stage having a second pitch that is greater than the first pitch; and
a second member comprising a head, a shaft and a neck positioned between the shaft and the head, an interface between the neck and the head defining a shoulder of the second member, the shaft comprising an outer surface defining a second thread configured to engage the first thread, the second thread having a uniform pitch along an entire length of the second thread, the neck comprising a smooth unthreaded first section and a second section comprising a plurality of teeth,
wherein the second member is unable to translate relative to the first member without rotating the second member relative to the first member when the second thread is positioned within the first stage,
wherein the second member is able to translate relative to the first member without rotating the second member relative to the first member when the second thread is positioned within the second stage and is spaced apart from the first stage,
wherein the shoulder is configured to engage the first thread when the second thread is positioned within the second stage and is spaced apart from the first stage such that engagement of the first thread with the shoulder and rotation of the second member relative to the first member causes the second member to axially translate in a proximal direction relative to the first member,
wherein the second thread form engages the first thread when the second member translates axially in the proximal direction relative to the first member to provisionally lock the second member with the first member, and
wherein a last one of the teeth includes a relief that is configured to be wedged into a minor diameter of the first thread when the second thread is positioned within the second stage and is spaced apart from the first stage to act as a final lock between the second member and the first member.

\* \* \* \* \*